(12) United States Patent
Kato

(10) Patent No.: US 7,065,392 B2
(45) Date of Patent: Jun. 20, 2006

(54) APPARATUS FOR EVALUATING BIOLOGICAL FUNCTION

(76) Inventor: Toshinori Kato, 18-6-402 Shirokanedai 5-chome Minato-ku, Tokyo (JP) 108-0071

(*) Notice: Subject to any disclaimer, the term of this patent is extended or adjusted under 35 U.S.C. 154(b) by 0 days.

(21) Appl. No.: 10/915,711

(22) Filed: Aug. 11, 2004

(65) Prior Publication Data

US 2005/0080323 A1   Apr. 14, 2005

Related U.S. Application Data

(63) Continuation of application No. PCT/JP03/01599, filed on Feb. 14, 2003.

(30) Foreign Application Priority Data

Feb. 14, 2002 (JP) ............................. 2002-037276

(51) Int. Cl.
 *A61B 5/00* (2006.01)
(52) U.S. Cl. .................................................. 600/323
(58) Field of Classification Search ................ 600/310, 600/322–323, 473
See application file for complete search history.

(56) References Cited

U.S. PATENT DOCUMENTS 6,587,703 B1 * 7/2003 Cheng et al. ............... 600/310
6,640,130 B1 * 10/2003 Freeman et al. ............ 600/474

FOREIGN PATENT DOCUMENTS

| JP | 09-149903 | 6/1997 |
| JP | 09-238914 | 9/1997 |
| JP | 2001-212115 | 8/2001 |

* cited by examiner

Primary Examiner—Eric F. Winakur
(74) Attorney, Agent, or Firm—Jacobson Holman PLLC

(57) ABSTRACT

The present invention provides an apparatus for evaluating biological function that, in differentiating as far as possible information from the capillaries, which reflects tissue metabolism, from information from outside the tissue (for example, the arteries and veins), has high speed and accuracy enabling it to compensate for the low spatial resolution of conventional near infrared spectroscopy methods, and that furthermore does not merely monitor changes in oxygen concentration and the like, but makes it possible to easily and conveniently distinguish between capillary reactions, metabolic reactions and the like; its configuration is characterized in that it provides a light irradiation means for irradiating light to a specified site of a living body, a light detection means for detecting light exiting from the living body, a calculation means for determining the respective changes in concentration of oxygenated hemoglobin and deoxygenated hemoglobin by performing calculations in near infrared spectroscopy with the intensity of the detected light as a parameter, and a display means for displaying information concerning the relative ratio "k" between both these data over time.

10 Claims, 11 Drawing Sheets

APPARATUS FOR EVALUATING BIOLOGICAL FUNCTION

This is a continuation of PCT/JP03/01599 filed Feb. 14, 2003 and published in Japanese.

TECHNICAL FIELD

The present invention relates to apparatus for evaluating biological function that measures changes in hemoglobin and the like in the blood based on light—such as transmitted, reflected, scattered or diffused light—from a living body detected by a photosensor after its interaction with the living body.

BACKGROUND ART

Since the time that a method whereby faint near infrared rays (700–1300 nanometers) are irradiated from on the skin of the head through the skull into the brain to measure changes in concentration of oxygenated hemoglobin (Oxy-Hb; $HbO_2$) and changes in concentration of deoxygenated hemoglobin (Deoxy-Hb; Hb) in the blood at the brain surface (cerebral cortex) just inside the skull was proposed by F. F. Jobsis in 1977, research on the measurement of tissue oxygen concentration by means of this near-infrared spectroscopy (NIRs) method has progressed rapidly.

The near-infrared spectroscopy method has the advantages that metabolism of separate tissues can be measured non-invasively (non-invasiveness), that this can furthermore be implemented with a simple and convenient apparatus (portability), and that, unlike PET (positron emission CT), f-MRI (functional magnetic resonance imaging) and the like, it additionally makes possible the real-time measurement of changes in tissue metabolism in the brain, muscles and the like over time (temporality); and it has given rise to expectations of a wide range of application, such as in monitoring brain function, evaluating muscle rehabilitation in physical therapy, and use in exercise physiology.

The present inventor and his colleagues conducted light stimulus experiments in humans in which the brain was partially irradiated with near infrared light, and as a result, showed that the distribution of localized brain function can be monitored at the bedside, and proved that imaging of local brain function using this bedside method of non-invasive detection of local brain function is possible (Toshinori Kato, Sachio Takashima, "NIR Spectroscopy ni yoru kyokusho nouketsuryu hendou no kansatsu", *Shinshinshougaiji(sha) no iryou ryouiku ni kansuru sougouteki kenkyu no houkokusho* ["Observation of variation in local brain blood flow by means of near-infrared spectroscopy", in *Comprehensive Research Report Concerning Medical Care for Children (People) with Disabilities*] (Japan Ministry of Health and Welfare), p. 179–181 (1992); Kato T, Kamei A, et al., "Human visual cortical function during photic stimulation monitoring by means of near-infrared spectroscopy", *J Cereb Blood Flow Metab.* 13:516–520 (1993). This is the pioneering work on the technology for graphic display of functional topography of the brain surface in the front and back of the head (the mapping of hemoglobin distribution, i.e., the display of variation in blood volume, reflecting brain activity, as a topographical map).

Examples of subsequent technology for the graphic display of brain function include the inventions described in Japan published patent applications No. H9-149903, No. 2001-212115 and No. H9-238914. The inventions described in these publications concern apparatus for measuring the interior of a living body by irradiating the living body with near infrared light from a plurality of irradiation sites and detecting light transmitted through the living body at a plurality of detection sites; this is called Optical Topography (registered trademark), and it calculates changes in concentration of oxygenated hemoglobin and deoxygenated hemoglobin in the blood at each measuring point, based on light intensity signals measured at a plurality of measuring points, and displays them topographically.

Because the oxygen partial pressure of the capillaries is approximately equal to that of the tissue, it is conventionally accepted that in measuring tissue oxygen concentration, it is extremely important to collect capillary blood oxygen concentration data. The near-infrared spectroscopy method, however, takes measurements non-invasively, from the surface of the body, and because changes in the signal are thus the sum of reactions occurring in the regions existing on the light path, its quantifiability, i.e., spatial resolution, is considered to be inferior. The data shown in FIG. 1(a) was conventionally accepted as predominantly capillary data, as clearly shown in the literature by H. Marc Watzman et al. ("Arterial and venous contributions to near-infrared cerebral oximetry", *Anesthesiology* 2000;93:947–53) and FIG. 8 of Japan published patent application H9238914, but the present inventor believes that this is inevitably predominantly venous data, by reason of the facts that it was obtained by measuring a site where a vein typically exists on the light path and that the apparatus was configured with wide spacing (approximately 30 mm) between the measuring points.

This is because the capillaries are structured in such a way that application of stimulus easily results in a divergence between red blood cell variation and blood serum component variation. Namely, in the capillaries, the red blood cells and the serum move at different speeds, changes in the hematocrit or changes in total hemoglobin are therefore more likely to occur there than in the veins, and consequently, mirror-image changes in oxygenated hemoglobin and deoxygenated hemoglobin are less likely to occur there than in the veins. Predominantly capillary data is therefore considered necessarily to be that in FIG. 1(b), which shows an asymmetrical mode of change, because of the conclusions obtained in the research of the present inventor. If this is the case, then conventional measuring apparatus can be said to be configured based on an erroneous theoretical understanding.

Additionally, even in the rare case when a conventional measuring apparatus recognizes the data shown in FIG. 1(b) as true predominantly capillary data, because the characteristics of change over time for both predominantly capillary data and predominantly venous data are macroscopically approximated before the application of stimulus (including both internal stimuli from physiological effects and external stimuli)—that is, at rest, before changes occur in the tissue (in the figures, baseline=the period up to approximately 8 seconds)—when this data is compared with the predominantly venous data of FIG. 1(a) it is impossible to tell whether the data being collected is predominantly capillary data or predominantly venous data during the period up until changes occur in the tissue, using a conventional measuring apparatus, which is confined to the output of FIGS. 1(a) and (b). Taking this time lag together with the extremely low probability of collecting capillary data because of the wide setting of the measuring point spacing (approximately 30 mm), gives rise to low expectations of a sufficient contribution to on-site medicine.

In addition, because conventional measuring apparatus only measure changes in oxygenated hemoglobin and deoxygenated hemoglobin concentration (and this data is highly inaccurate), and because theories of brain physiology, such as the interrelationships between these data and vasodilatation/vasoconstriction occurring in the capillaries, and the involvement of hematocrit changes and the oxygen extraction rate in the capillaries accompanying changes in total hemoglobin, have not been adequately clarified, these apparatus therefore remain in the realm of simple scientific experimental tools, as monitors showing changes in concentration of hemoglobin and the like, and monitors showing changes in oxygen concentration.

The present invention accordingly takes into consideration the above-stated problems, and takes as its subject the provision of an apparatus for evaluating biological function that, in differentiating as far as possible information from the capillaries, which reflects tissue metabolism, from information from outside the tissue (for example, the arteries and veins), has high speed and accuracy enabling it to compensate for the low spatial resolution of conventional near infrared spectroscopy methods, and that furthermore does not merely monitor changes in oxygen concentration and the like, but makes it possible to easily and conveniently distinguish between capillary reactions, metabolic reactions and the like.

DISCLOSURE OF THE INVENTION

In order to resolve the problems described above, the apparatus for evaluating biological function of the present invention is characterized in that it provides a light irradiation means for irradiating light to a specified site of a living body, a light detection means for detecting light exiting from the living body, a calculation means for determining the respective changes in concentration of oxygenated hemoglobin and deoxygenated hemoglobin by performing calculations in near infrared spectroscopy with the intensity of the detected light as a parameter, and a display means for displaying information concerning the relative ratio "k" between both these data over time.

The above configuration makes it possible to determine promptly, according to physiological theory, whether that data is predominantly capillary data, even in a resting state when no stimulus of any kind is applied to the tissues of the living body, by evaluation of the relative ratio "k". Namely, because it is clear that if capillary data, the relative ratio "k" will be near to −1, and if venous data, the relative ratio "k" will be somewhat off from −1 on the plus side, whether the data is predominantly capillary data is determined by whether or not the value of the relative ratio "k" is in the vicinity of −1.

Additionally, the apparatus for evaluating biological function of the present invention more preferably employs a configuration in which the light detection means detects light exiting from the living body at a plurality of detection sites, and the calculation means is capable of determining the respective changes in concentration of oxygenated hemoglobin and deoxygenated hemoglobin at each detection site, as set forth in claim 2. If the fact that the probability of collecting predominantly capillary data is low is taken into consideration, increasing the number of detection sites provides greater reliability. However, when the irradiation site and the detection site are somewhat separated, noise, such as that from veins, is likely to occur, and so the space between the irradiation site and the detection site is therefore preferably as small as possible. When measuring two or more histologically independent sites, a plurality of pairs of irradiation means and detection means may be prepared corresponding to the measurement sites.

Furthermore, the apparatus for evaluating biological function of the present invention can employ a configuration that further provides a decision means for identifying, by deciding whether the relative ratio "k" satisfies the condition $k \leq -0.8$ (more preferably $k \leq -0.9$; these take into consideration deflection errors of k), those detection sites for which the decision result is yes; and a selection means for invalidating detection sites for which the decision result is no, by means of the input of information concerning these detection sites, as set forth in claim 3. This configuration makes it possible to reduce the processing load on the decision means by feeding decision results back into the selection means to reduce the amount of data processed.

Additionally, the apparatus for evaluating biological function of the present invention can employ a configuration in which the display means displays information concerning the relative ratio "k" as a two-dimensional diagram plotted over time, as set forth in claim 4. Displaying changes in the relative ratio "k" over time plotted in a two-dimensional diagram makes it possible to perform evaluations of biological function based on the characteristics of changes in the plot locus over time.

As described above, the apparatus for evaluating biological function of the present invention, by elucidating the physiological adjustment functions of the capillaries to derive the concept of a ratio between the change in oxygenated hemoglobin concentration and the change in deoxygenated hemoglobin concentration, achieves high speed and accuracy in distinguishing, as far as possible, information from the capillaries, which reflects tissue metabolism, from information from outside the tissue (for example, the arteries and veins), enabling it to compensate for the low spatial resolution of conventional near infrared spectroscopy methods. Additionally, evaluation of this ratio makes it possible not only to monitor changes in oxygen concentration, but also to easily and conveniently track capillary reactions and in turn tissue metabolism reactions, and thus implement the evaluation of biological function.

BEST MODE FOR CARRYING OUT THE INVENTION

One working embodiment of the apparatus for evaluating biological function of the present invention is described below, with reference to the drawings.

Figure 2A:
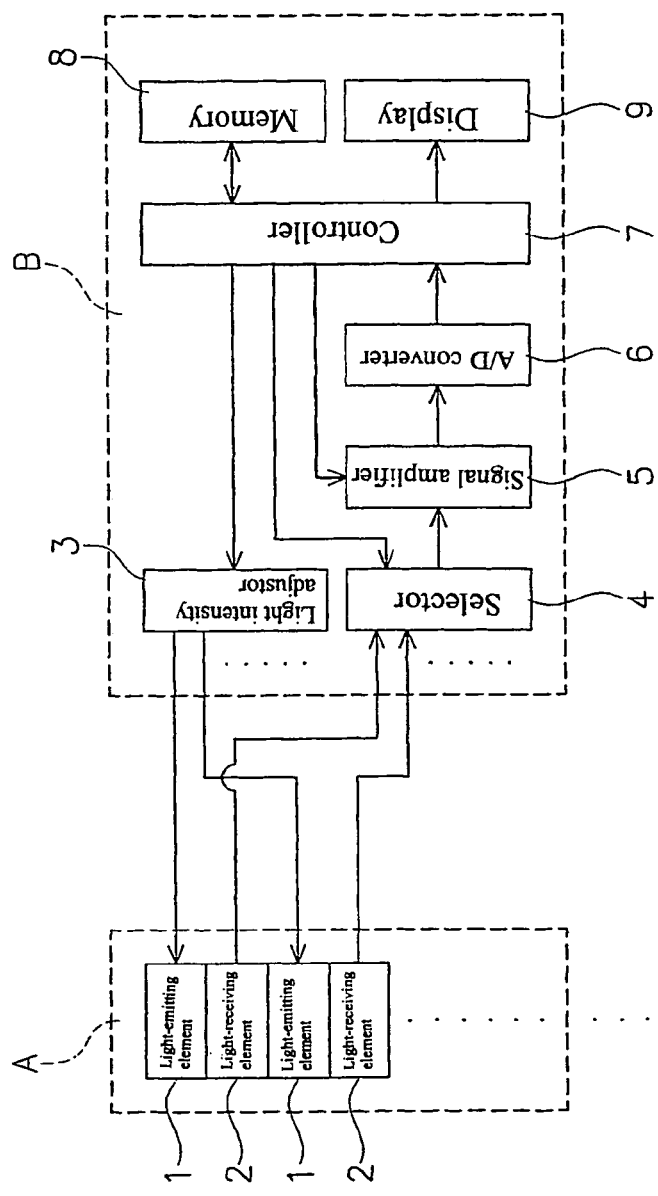
In FIG. 2, (a) shows a block diagram of the apparatus for evaluating biological function of the present working embodiment, and (b) shows a pattern of arrangement of light emitters and light receptors in a probe of the present working embodiment.

FIG. 2(a) shows a block diagram of the apparatus for evaluating biological function of the present working embodiment. This apparatus for evaluating biological function is roughly divided into a plurality of probes A . . . and the main body of the apparatus B. Probe A is composed of at least two light-emitting elements (light-emitting diodes) 1 . . . that irradiate light to desired measurement sites (tissue) of a living body, and at least two light-receiving elements (photodiodes) 2 . . . that sense light, e.g., transmitted, reflected, scattered or diffused light, from the measurement site after it has interacted with the living body. The main body of the apparatus B is composed of a light intensity adjustor 3 that adjusts the intensity of the light emitted from light-emitting elements 1 . . . ; a selector 4 that selectively validates (invalidates) desired light-receiving elements 2 . . . ; a gain controllable signal amplifier 5 that amplifies the signals from light-receiving elements 2 . . . ; an A/D converter 6 that converts the output from signal amplifier 5 into numerical values; a controller 7 that executes specified operational processing based on feedback from each part of the apparatus, output from A/D converter 6, and the like; a memory 8 that is used to record output from A/D converter 6, control data from each part of the apparatus, calculated results or the like; and a display 9 that implements displays based on results output from A/D converter 6, calculated results, and the like.

Figure 2B:
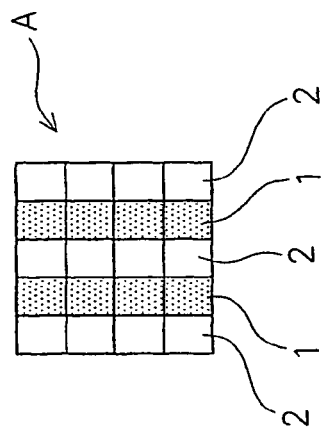
Figure 3A:
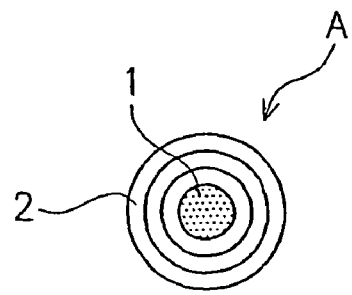
FIG. 3 shows arrangement patterns of light emitters and light receptors in probes; (a) is Variation 1, (b) is Variation 2, (c) is Variation 3, and (d) is Variation 4.
Figure 3B:
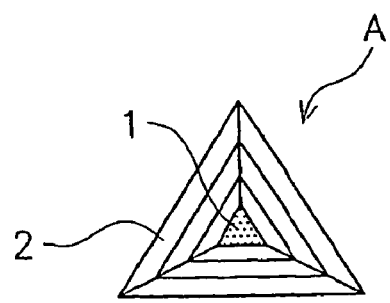
Figure 3C:
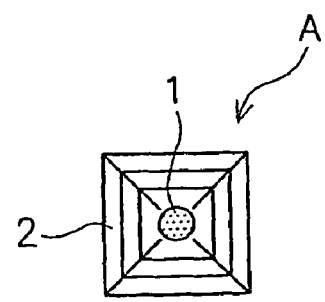
Figure 3D:
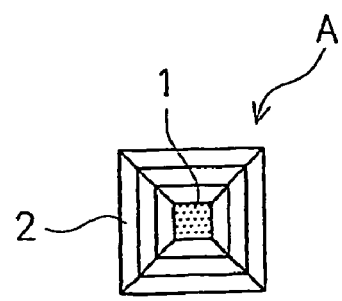

Light-emitting elements 1 . . . and light-receiving elements 2 . . . are disposed in matrix form with a plurality of columns and a plurality of rows (4×5 in the present working embodiment, disposed in such a way that light-emitting elements 1 and light-receiving elements 2 alternate; more specifically, in such a way that row[s] comprising only light-emitting elements 1 . . . and row[s] comprising only light-receiving elements 2 . . . are disposed alternately in the column direction), incorporated together as probe A, as shown in FIG. 2(b). Probes in conventional near-infrared topography apparatus were provided with a plurality of light irradiating probes and light detecting probes each having a thickness of ≧1 mm, disposed at intervals ≧25 mm, but in probe A of the present working embodiment, a plurality of multi-layer probes are provided, into each of which is tightly bundled a plurality of light-emitting elements 1 . . . and light-receiving elements 2 . . . to the small size of a square ≦3 mm on a side (if round, ≦3 mm in diameter), to improve the probability of accurately detecting only the capillary regions; these are each independently disposed to correspond to the respective measurement sites; and because the surface area measured is reduced, they can be applied not only to the brain, but also to the skin and internal organs (in this case, a probe of an embodiment adapted to an endoscopic mode of use is used).

The external shape of the tip of probe A (the part that comes in contact with the measuring site), and the angles of the emission surface of each light-emitting element and the incident surface of the light-receiving surface of each light-receiving element 2 . . . are determined according to such factors as the surface shape of each site—the nails, the palm of the hand, the bottom of the foot, the ear lobe, etc.—and the purpose of the probe. Probe A may also be a multilayer probe, shaped, for example, like a light bulb or in a geometrical shape, constructed like those shown in FIG. 3, in which a plurality of light-receiving elements 2 . . . are disposed around at least 1 light-emitting element. These shapes are determined with an endoscopic mode of use in view, such as for the mouth and digestive system, or the respiratory system.

In FIG. 2(b), two types of light-emitting elements 1 . . . are provided, those irradiating light of 730 nm wavelength and those irradiating light of 850 nm wavelength. These are disposed, for example, alternately in the row direction, but when considering other possible patterns, it is important to take into consideration wavelength-dependent attenuation inside the tissue, and dispose them in such a way that the amount of light received can be measured in a balanced way. All the light-emitting elements 1 . . . are connected to light intensity adjuster 3, and the intensity of the emitted light can be adjusted either overall or individually.

Meanwhile, all the light-receiving elements 2 . . . are connected to signal amplifier 5 through selector 4, and the received light signal output from each light-receiving element 2 is output to signal amplifier 5, either from all of them or partially, as selected by selector 4, and amplified here. Then, the amplified received light signals are converted to numeric values by A/D converter 6 and output to controller 7. Controller 7, after applying a low pass filter to the digital data input from A/D converter 6 to eliminate noise, records this processed data (referred to below as "received light intensity") chronologically in memory 8.

Additionally, controller 7 executes the operations described below based on the received light intensity thus obtained. As the first step, it calculates absorbance at 730 nm wavelength (O.D.$_{730}$) by means of Equation 1 and absorbance at 850 nm wavelength (O.D.$_{850}$) by means of Equation 2, and records the results of these calculations chronologically in memory 8.

$$O.D._{730} = \log_{10}(I_{0\;730}/I_{730}) \quad \text{(Equation 1)}$$

$$O.D._{850} = \log_{10}(I_{0\;850}/I_{850}) \quad \text{(Equation 2)}$$

where:

$I_{0\;730}$ is emitted light intensity at 730 nm wavelength, $I_{730}$ is received light intensity at 730 nm wavelength, $I_{0\;850}$ is emitted light intensity at 850 nm wavelength, and $I_{850}$ is received light intensity at 850 nm wavelength.

From theory known in the art, the relationships expressed by Equations 3 and 4 are known to exist between change in oxygenated hemoglobin concentration, change in deoxygenated hemoglobin concentration, and change in absorbance.

$$\Delta O.D._{730} = a_1 \Delta[HbO_2] + a_1' \Delta[Hb] \quad \text{(Equation 3)}$$

$$\Delta O.D._{850} = a_2 \Delta[HbO_2] + a_2' \Delta[Hb] \quad \text{(Equation 4)}$$

where:

A O.D.$_{730}$ is change in absorbance at 730 nm wavelength,
ΔO.D.$_{850}$ is change in absorbance at 850 nm wavelength
Δ[HbO$_2$] is change in oxygenated hemoglobin concentration
Δ[Hb] is change in deoxygenated hemoglobin concentration, and
$a_1, a_1', a_2, a_2'$ are absorbance coefficients.

From these simultaneous equations known in the art, Equations 5 and 6 can be solved.

$$\Delta[HbO_2]=a\{\Delta O.D._{730}-(a_1'/a_2')\Delta O.D._{850}\} \quad \text{(Equation 5)}$$

$$\Delta[Hb]=a(a_2/a_2')\{(a_1/a_2)\Delta O.D._{850}-O.D._{730}\} \quad \text{(Equation 6)}$$

where:

$$a=a_2'/(a_1a_2'-a_1'a_2)\approx 1 \text{ (1 or a value approaching 1)}$$

Accordingly, after determining, as the second step, the change in absorbance at 730 nm wavelength (ΔO.D.$_{730}$) and the change in absorbance at 850 nm wavelength (ΔO.D.$_{850}$), as the third step, the change in oxygenated hemoglobin concentration (Δ[HbO$_2$]) is calculated by means of Equation 5 and the change in deoxygenated hemoglobin concentration (Δ[Hb]) by means of Equation 6, and the results of these calculations are recorded chronologically in memory 8. The change in total hemoglobin concentration (Δ[total Hb]) is represented by Equation 7.

$$\Delta[total\ Hb]=\Delta[HbO_2]+\Delta[Hb] \quad \text{(Equation 7)}$$

The changes in concentration of oxygenated hemoglobin and deoxygenated hemoglobin in the capillaries induced by stimulus to the tissues show the 9 patterns of change below, according to the possible combinations of their variation.

(1) ΔHbO$_2$: increase; ΔHb: increase
(2) ΔHbO$_2$: increase; ΔHb: decrease
(3) ΔHbO$_2$: increase; ΔHb: zero
(4) ΔHbO$_2$: decrease; ΔHb: increase
(5) ΔHbO$_2$: decrease; ΔHb: decrease
(6) ΔHbO$_2$: decrease; ΔHb: zero
(7) ΔHbO$_2$: zero; ΔHb: increase
(8) ΔHbO$_2$: zero; ΔHb: decrease
(9) ΔHbO$_2$: zero; ΔHb: zero.

In actuality, with metabolic activity in the tissues, the above patterns are changing over time according to such factors as differences in stimulus application conditions and the physiological state at rest. Δ[Hb] and Δ[HbO$_2$] in the capillaries fluctuate with blood flow and metabolic activity for the purpose of taking oxygen up into the tissue from oxygenated hemoglobin. The ratio between the respective changes in concentration of oxygenated hemoglobin and deoxygenated hemoglobin in the capillaries is thus shown to be an important parameter reflecting tissue blood flow and metabolism. Accordingly, as the fourth step, this ratio (referred to below as the "tissue oxygen exchange ratio" or "k"), is calculated according to Equation 8.

$$k=\Delta[Hb]/\Delta[HbO_2] \quad \text{(Equation 8)}$$

where:

k is the tissue oxygen exchange ratio.

The tissue oxygen exchange ratio is represented, for example in the brain blood vessel metabolism system, by Equation 9.

$$k=(1-h)/\{h+Y/(1-Y)\} \quad \text{(Equation 9)}$$

where:

Y is blood oxygen saturation $$h=(1-\beta+\gamma)/\alpha \quad \text{(Equation 10)}$$

α, β and γ are indices representing the relationships shown below between regional blood flow (rBF), and hemoglobin volume (v), oxygen extraction (OE) and hematocrit (Ht).

$$v=c_1 \cdot rBF\alpha \quad \text{(Equation 11)}$$

$$OE=c_2 \cdot rBF\beta \quad \text{(Equation 12)}$$

$$Ht=c_3 \cdot rBF\gamma \quad \text{(Equation 13)}$$

Consequently, the tissue oxygen exchange ratio can be evaluated as an index that fluctuates according to regional blood flow (rBF) on the one hand, and hemoglobin volume (v), oxygen extraction (OE) and hematocrit (Ht) on the other.

Controller 7 records processed data (values of k), obtained by executing the operations in the above-mentioned steps 1 through 4, chronologically in memory 8. One objective of the apparatus for evaluating biological function of the present working embodiment is to determine this tissue oxygen exchange ratio, but by expressing this tissue oxygen exchange ratio as a two-dimensional diagram, in which the horizontal axis shows the change in oxygenated hemoglobin concentration and the vertical axis shows the change in deoxygenated hemoglobin concentration, it becomes a valid diagnostic ingredient for evaluating biological function. Display 9 receives display data transmitted from controller 7 and displays it as diagrams such as that shown in FIG. 4. Display content other than these diagrams may include information related to emitted light intensity, absorbance, concentration, and tissue oxygen exchange ratios, including graphs representing changes in concentration over time, such as those shown in FIG. 1.

Figure 1A:
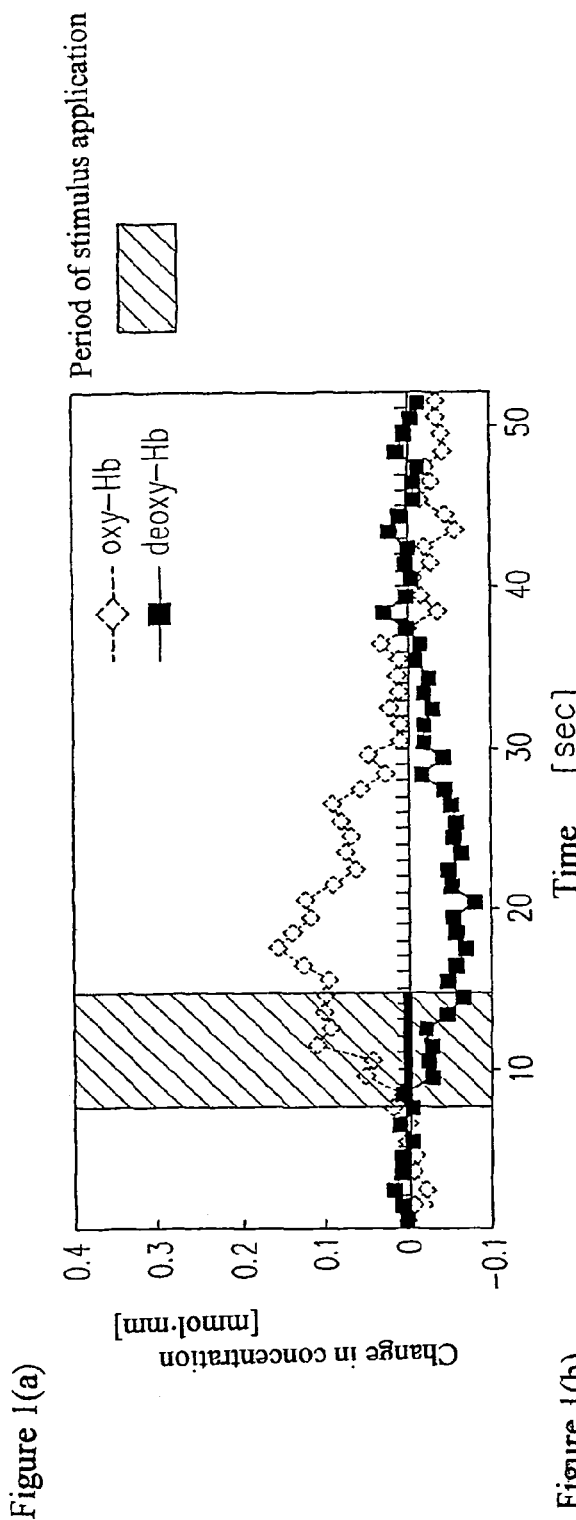
FIG. 1 shows characteristic graphs showing changes in hemoglobin concentration vs. time; (a) shows predominantly venous data (conventionally accepted as predominantly capillary data), and (b), predominantly capillary data.
Figure 1B:
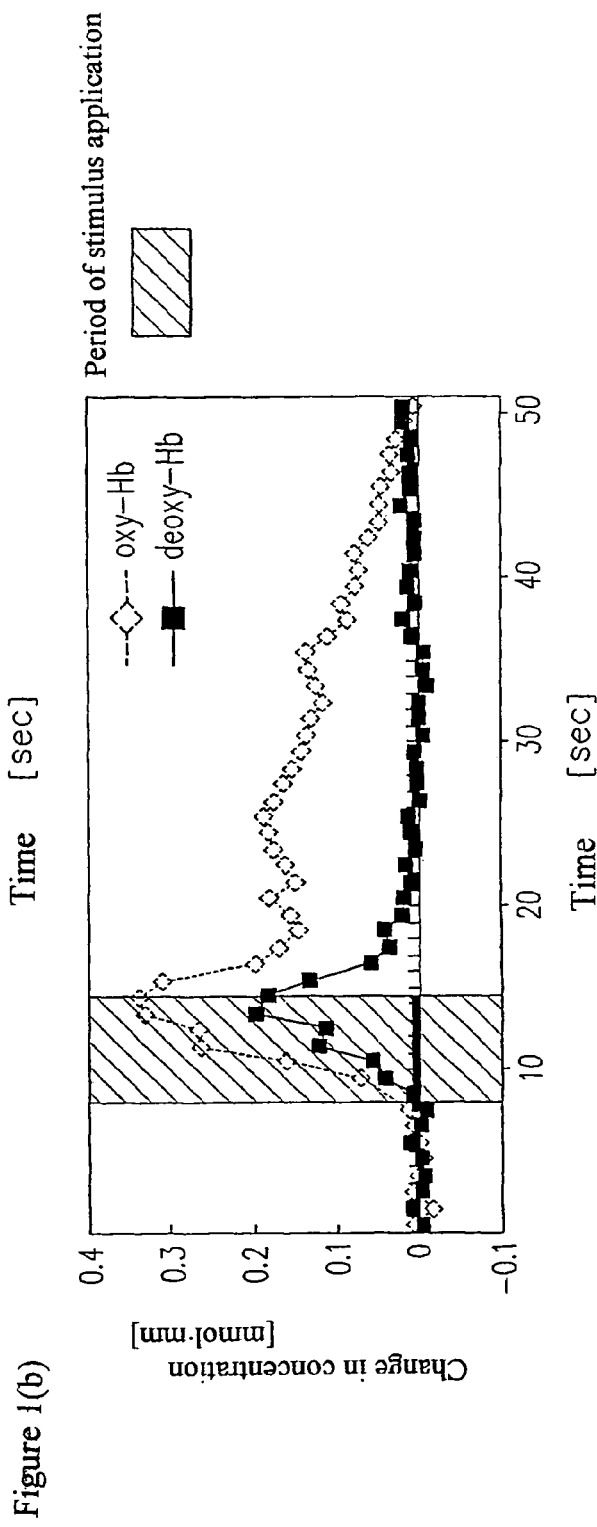
Figure 4:
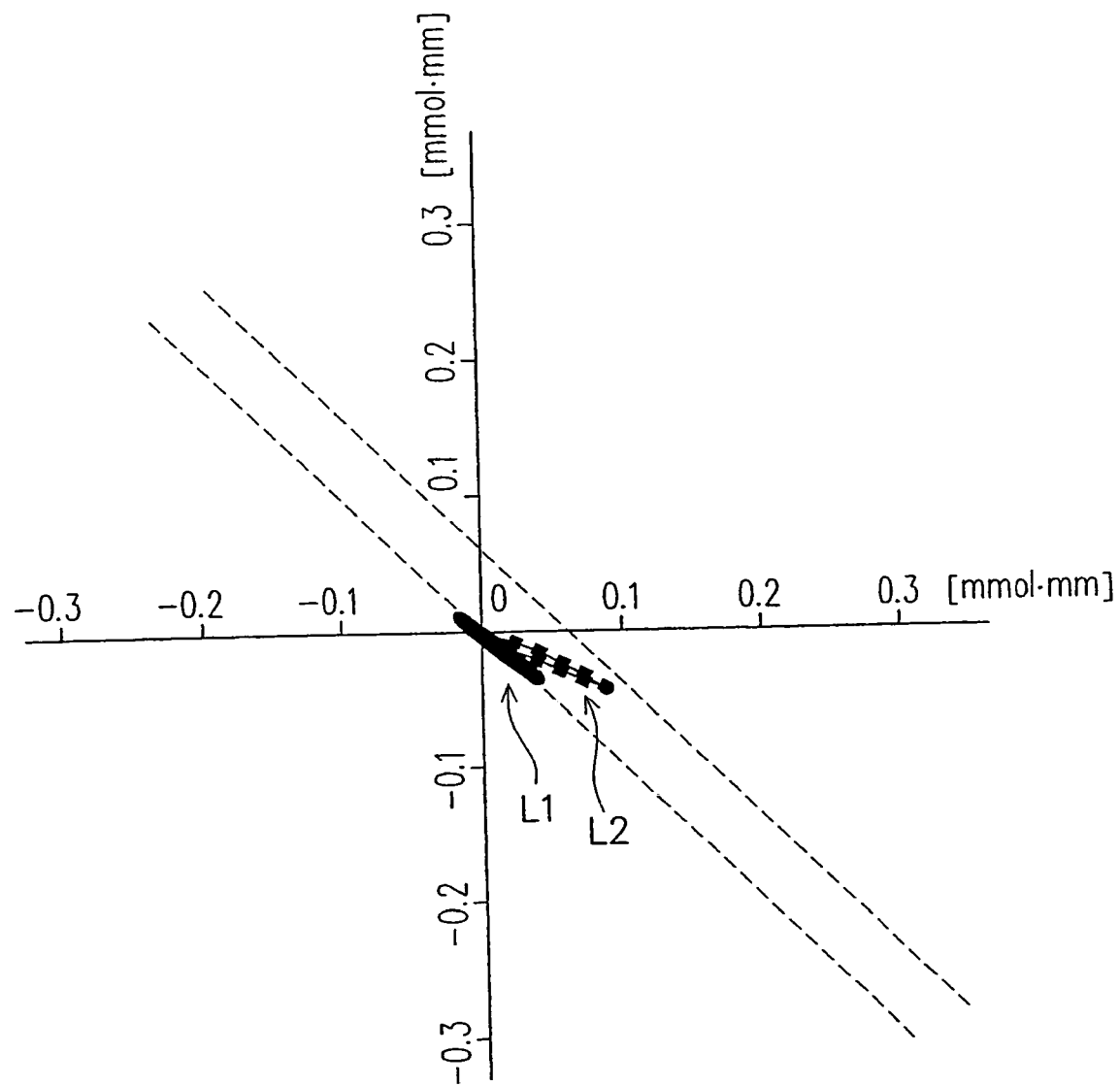
FIG. 4 is a diagram on the display obtained by plotting calculated results over time; it shows predominantly capillary data and predominantly venous data before stimulus is applied to the tissue.

FIG. 4 shows a diagram of the baseline period of FIG. 1, (before the period when stimulus is applied), obtained by plotting Δ[HbO$_2$] on the X-axis (horizontal) and Δ[Hb] on the Y-axis (vertical). The predominantly capillary and predominantly venous baseline loci each show repeated back-and-forth motion within the same range, with different values of k (slope). If the slope of the baseline locus is close to 45 degrees (L1 in the figure), the data collected from the measurement site is predominantly capillary data (necessary data, because it reflects tissue metabolism), and if the slope of the locus is closer to zero degrees (L2 in the figure), it is predominantly venous data (unnecessary data).

The reason that the slope of the baseline locus differs according to whether it is predominantly capillary or predominantly venous is based on differences in physiological adjustment in the capillaries and in the veins. It is known that in the capillaries, in order to pass through capillaries of approximately 5 μM, red blood cells of approximately 7 μm are deformed. In the veins, which have larger vessel diameters and expand easily and passively, there is no need for the red blood cells to deform. Namely, fluctuations in total blood volume (serum and blood cells) are less likely to occur in the capillaries than in the veins. As recognized in the literature by Johnson et al. (Johnson P C, Blasche J, Burton K S and Dial J H 1971 "Influence of flow variations on capillary hematocrit in mesentery", *Am. J. Physiol.* 221 105–12) and others, the blood flow velocity and the hematocrit are proportional; and because the blood flow velocity is adjusted precisely, adjustment occurs to maintain the total hemoglobin at a constant level even if some fluctuation in blood flow velocity occurs, and the range of variation is small and the slope of the baseline locus is near minus 45 degrees at rest. However, on the venous side, the structure of the blood vessels is different, and fluctuations in blood flow velocity occur with difficulty, while fluctuations in total blood volume occur easily, because of changes in pressure from the arterial side. There is consequently a tendency towards a slight increase in oxygenated hemoglobin over deoxygenated hemoglobin, and the slope is off from minus 45 degrees.

Accordingly, from among the data obtained from all the light-receiving elements 2 . . . , controller 7 extracts the data that fulfils the condition of equation 14 and identifies the light-receiving element[s] 2 that output this data (more accurately, the received light intensity on which this data is based).

$$k > -0.8 \quad \text{(Equation 14)}$$

The light-receiving elements 2 . . . identified in this decision processing are the light-receiving elements 2 that measure the kind of sites where veins exist on the light path, and because they collect predominantly venous data, controller 7 outputs a non-select signal to selector 4, instructing selector 4 not to process (output to signal amplifier 5) the output from the specified light-receiving elements 2 . . . Alternatively, in view of the fact that if an evaluator looks at the diagram on display 9, it can be promptly determined even in the tissue resting state whether or not the data is predominantly capillary data, an external input means may be established connected to controller 7, and light-receiving elements 2 corresponding to unnecessary data as confirmed from the diagram on display 9 may be manually unselected by means of the external input means.

In this way, the apparatus for evaluating biological function of the present working embodiment can tell the difference in the respective behavior of predominantly capillary data and predominantly venous data at rest, and can automatically distinguish between those light-receiving elements 2 that collect predominantly capillary data and those light-receiving elements 2 that collect predominantly venous data even before tissue stimulation. Because the operations in steps 1 through 4 are not executed on unnecessary data, or in other words, because the amount of data to which the operations of steps 1 through 4 are applied is reduced, the processing load of controller 7 is lightened and high-speed processing is secured, while at the same time it is possible to collect only valid diagnostic material, and evaluation of biological function, described below, can be properly implemented.

Figure 5:
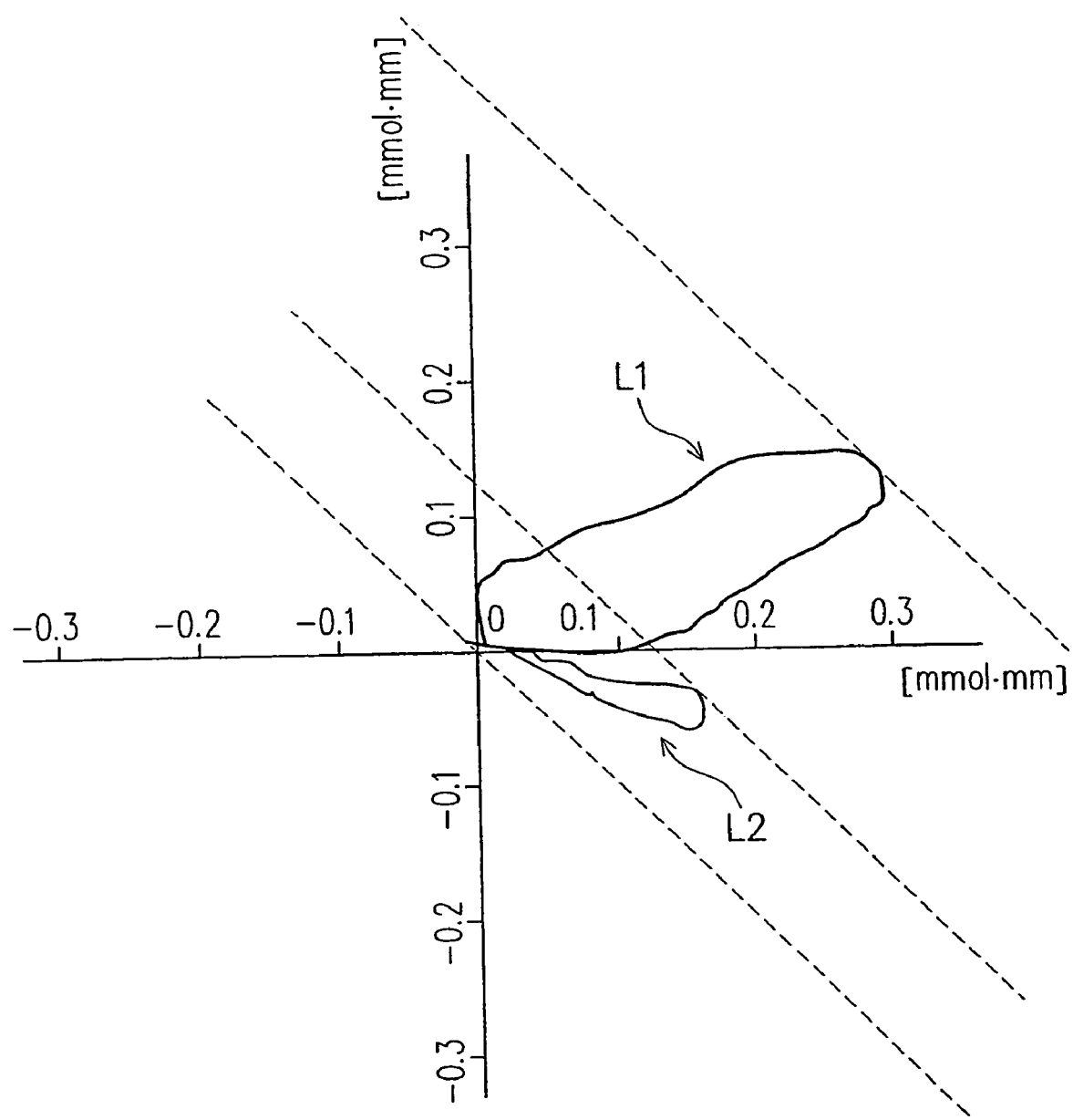
FIG. 5 is a diagram on the display obtained by plotting calculated results over time; it shows predominantly capillary data and predominantly venous data when stimulus is applied to the tissue.

FIG. 5 shows a diagram of the period in which stimulus is applied to FIG. 1. When the tissue enters an active state by means of stimulation, change is likely to occur predominantly as an increase in $\Delta[HbO_2]$, and because after the blood vessels expand, they contract, and, rarely, after contracting, they expand and contract repeatedly, the predominantly capillary and predominantly venous loci each shift from a back-and-forth motion to a circular motion.

The shape of the circular motion differs, however, according to whether it is predominantly capillary or predominantly venous. Because in the capillaries, stimulation causes the increase in serum due to increased blood flow velocity to exceed the increase in blood cells, thus increasing the hematocrit, total hemoglobin is likely to increase, and a shift into an asymmetrical pattern of variation of the above-mentioned type (1), "$\Delta[HbO_2]$: increase; $\Delta[Hb]$: increase" (L1 in the figure) is likely. In the veins, because venous blood is pushed out by inflowing arterial blood (predominantly oxygenated hemoglobin), total hemoglobin is unlikely to increase, and a symmetrical mirror-image pattern of variation of the above-mentioned type (2), "$\Delta[HbO_2]$ increase; $\Delta[Hb]$: decrease" is likely to occur (L2 in the figure). Additionally, the maximum distance from the zero point to L [$L^2=(\Delta[HbO_2])^2+(\Delta[Hb])^2$] is greater for the capillaries.

<Evaluation of Two-dimensional Diagrams>

The apparatus for evaluating biological function of the present working embodiment provides the following valid diagnostic materials (information on biological function), premised on the accurate extraction of predominantly capillary data reflecting tissue metabolism.

Figure 6:
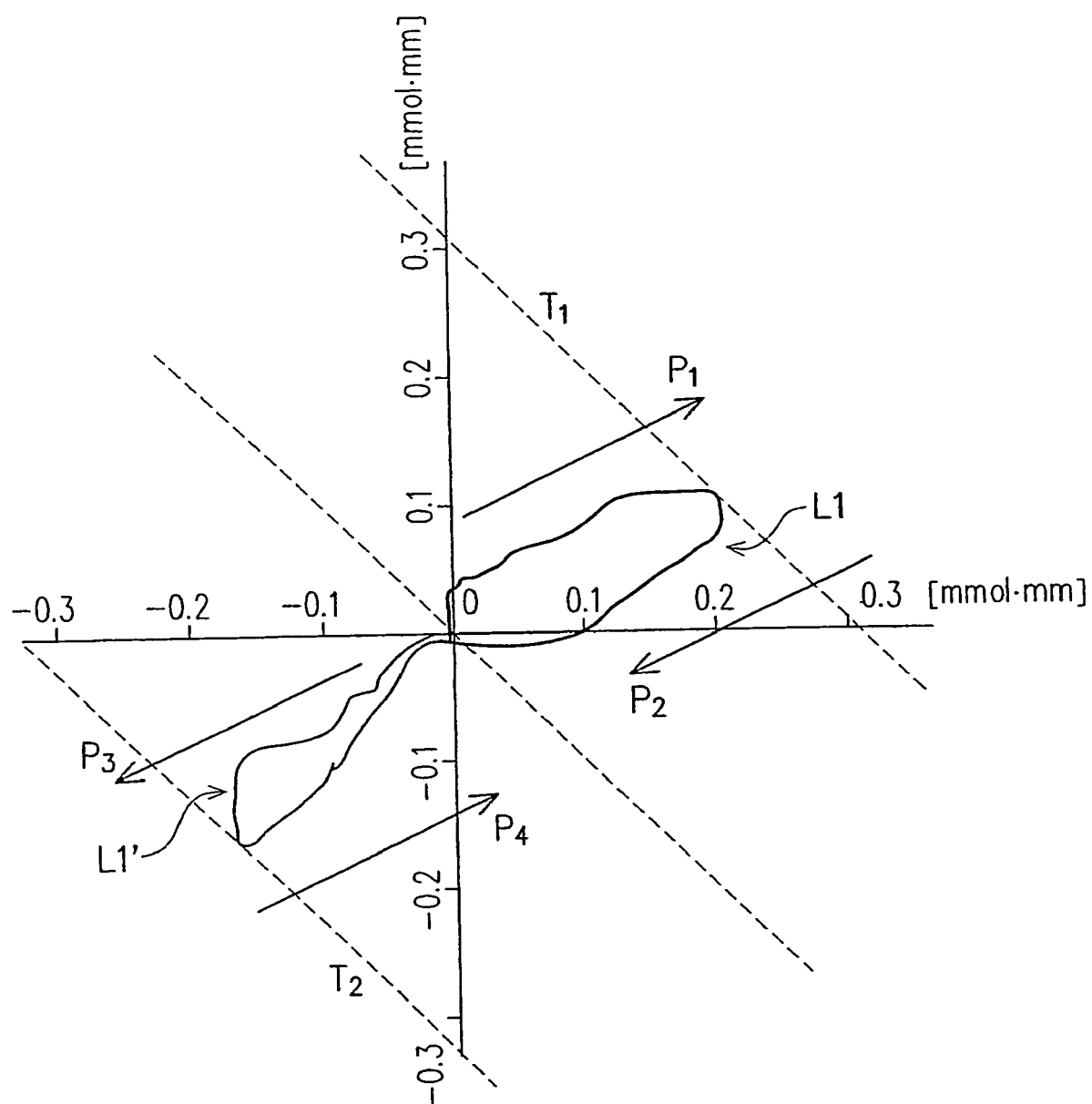
FIG. 6 is a diagram on the display obtained by plotting calculated results over time it shows predominantly capillary data when the capillaries are expanding and contracting.

The first point is information concerning the expansion and contraction of the capillaries at the measurement site. As stated above, the change in total hemoglobin concentration is the sum of the change in oxygenated hemoglobin concentration and the change in deoxygenated hemoglobin concentration, and it can be understood that if the total hemoglobin concentration tends to increase (i.e., $\Delta[total-Hb]>0$), the capillaries are expanded, and if, on the other hand, the total hemoglobin concentration tends to decrease (i.e., $\Delta[total-Hb]<0$), the capillaries are contracted. Namely, in FIG. 6, the circular plot locus L1 shows a situation in which the capillaries are expanded, and the circular plot locus L1' shows a situation in which the capillaries are contracted. If the plot locus L1 shows expansion in the direction of P1, it can be seen that the capillaries are in the process of expanding, and if it shrinks in the direction of P2, it can be seen that the capillaries are in the process of returning to their normal state. If the change in total hemoglobin concentration is zero, the capillaries are in their normal state. And, if plot locus L1' shows expansion in the direction of P3, it can be seen that the capillaries are in the process of contracting, and if it shrinks in the direction of P4, it can be seen that the capillaries are in the process of returning to their normal state. In this way, diagramming changes in the value k over time makes it possible to ascertain not only the state of the capillaries, but also real time shifts over time in the expansion and contraction functions.

The second point is information concerning maximum (minimum) change in total hemoglobin concentration. The points at which lines T1 and T2, which are tangential to the circular motion of the diagram and parallel to the slope of the baseline, intersect the Y axis represent the maximum (minimum) change in total hemoglobin concentration. This is because tangent T1 is represented by y=−x+a, and thus the maximum value a=x+y=maximum change in total hemoglobin concentration; and in the same way, tangent T2 is represented by y=−x−b, and thus the minimum value b=−(x+y)=minimum change in total hemoglobin concentration. Namely, the continuous correspondence or correlation between change in total hemoglobin and the expansion and contraction of the capillaries—total hemoglobin and hematocrit increasing, on the one hand, during the capillary expansion process while decreasing during the capillary contraction process—can be clearly understood from the diagrams.

Figure 7:
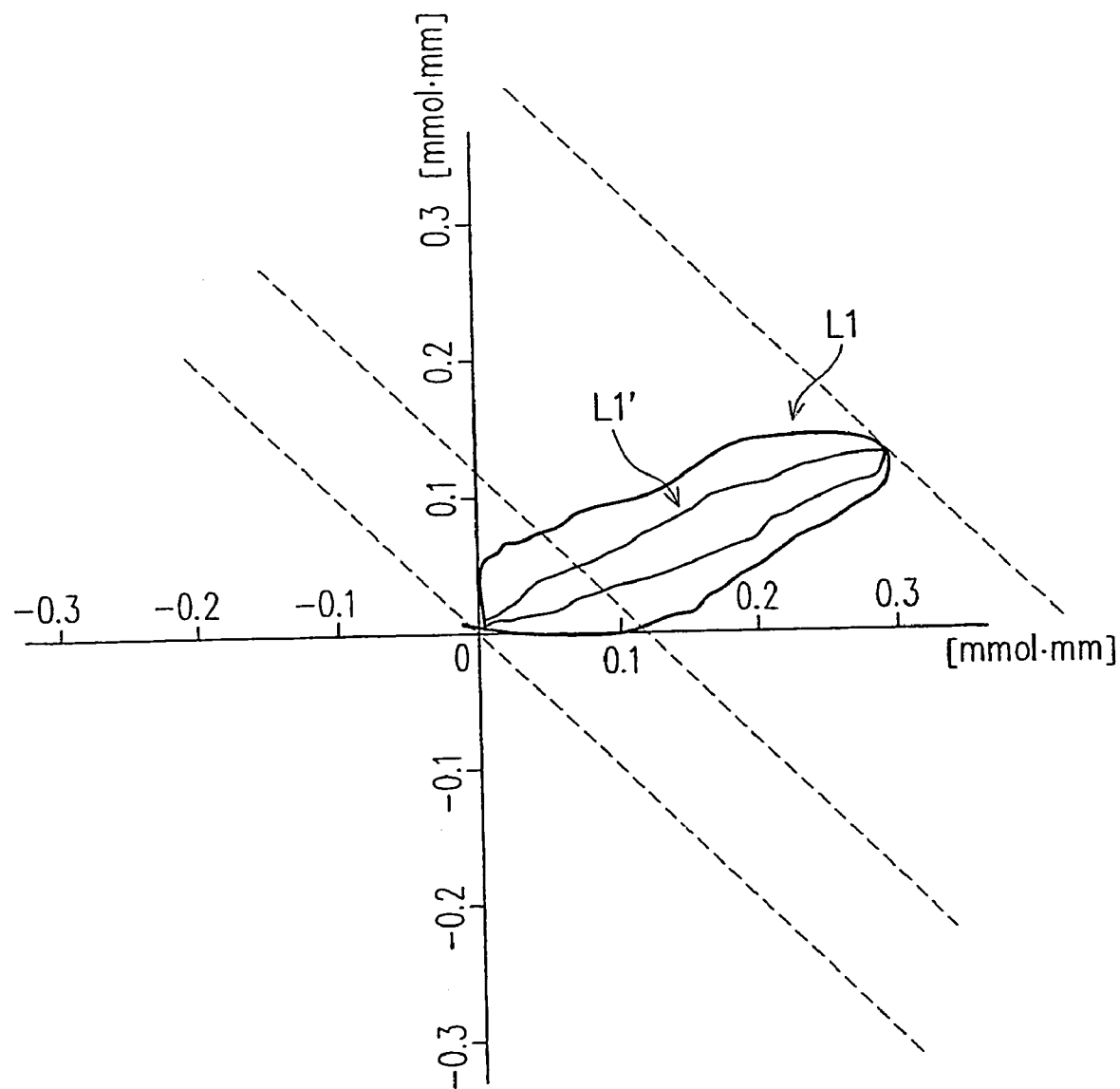
FIG. 7 is a diagram on the display obtained by plotting calculated results over time; it shows predominantly capillary data when stimuli of different intensities are applied to the capillaries.

The third point is information concerning the strength of stimulus applied to the tissue. In the diagram shown in FIG. 7, plot locus L1 shows a situation in which a stimulus of certain conditions is applied to the tissue, and plot locus L2 shows a situation in which a weaker stimulus than that of plot locus L1 is applied. This means that the larger the area of the circular region surrounded by the plot locus, the greater the strength or the longer the duration of the stimulus applied to the tissue. This is true, however, when the stimulus applied to the tissue is relatively strong or longlasting, but the situation differs when the stimulus applied is relatively weak (this will be described below).

Figure 8A:
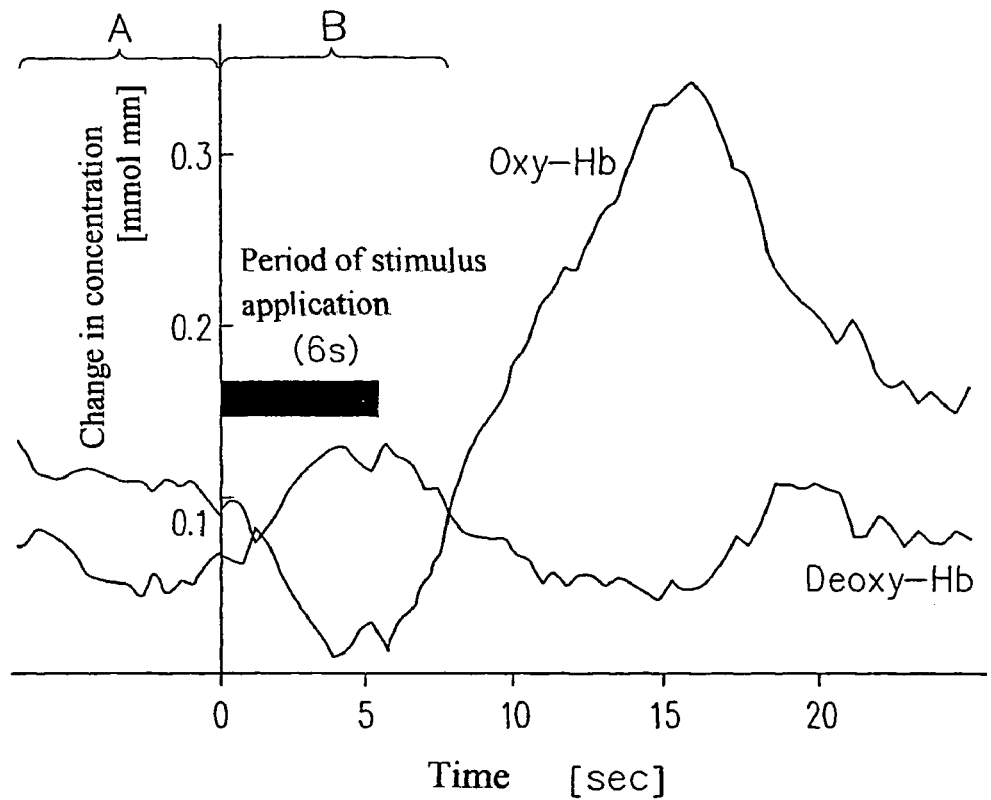
FIG. 8 shows predominantly capillary data before and after stimulus is applied to tissue; (a) is a characteristic graph showing changes in hemoglobin concentration over time, and (b) is a diagram on the display obtained by plotting those calculated results over time.
Figure 8B:
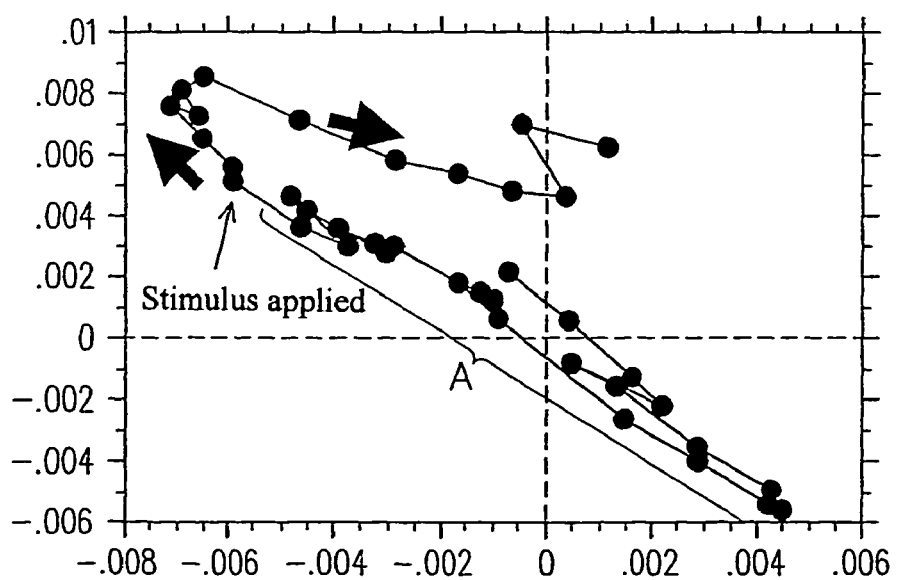

The fourth point is information concerning the starting point of the application of stimulus to the tissue. As shown in FIG. 8(a), when compared to the amplitude at the baseline (region A), the pattern of variation from the start of stimulation (region B) up to a few seconds later is similar to that of the baseline, and thus changes cannot be detected immediately after the start of stimulation merely by looking at changes in concentration of either deoxygenated hemoglobin or oxygenated hemoglobin. In actuality, for changes in brain blood flow, it was generally thought that it takes a few seconds after the start of stimulation until the blood flow increases. That is, changes could not be detected for 1–2 seconds while it passed through the capillaries. However, if displayed as a two-dimensional diagram, as shown in FIG. 8, it becomes possible to trace changes in blood flow and metabolic function in the order of milliseconds, because the start of the stimulus causes the slope/vector of the plot to change sharply from the baseline, making it possible to detect metabolic processes in the capillaries promptly.

The fifth point is information concerning the oxygen extraction rate and capillary oxygen saturation. In the capillaries, when the applied stimulus is relatively weak, the circular locus does not shift into the upper right region, but if the stimulus is strong, the stronger the stimulus, the further that locus shifts to the upper right. At the same time, as the locus extends further into the upper right region, the increase in the deoxygenated hemoglobin concentration accompanying the increase in oxygenated hemoglobin concentration becomes even greater, showing that the oxygen extraction rate has become very high. Furthermore, in the upper left region, where increased deoxygenated hemoglobin concentration accompanies decreased oxygenated hemoglobin, a drop in capillary oxygen saturation is shown.

<Examples of Evaluation Using the Apparatus (1)>

Figure 9:
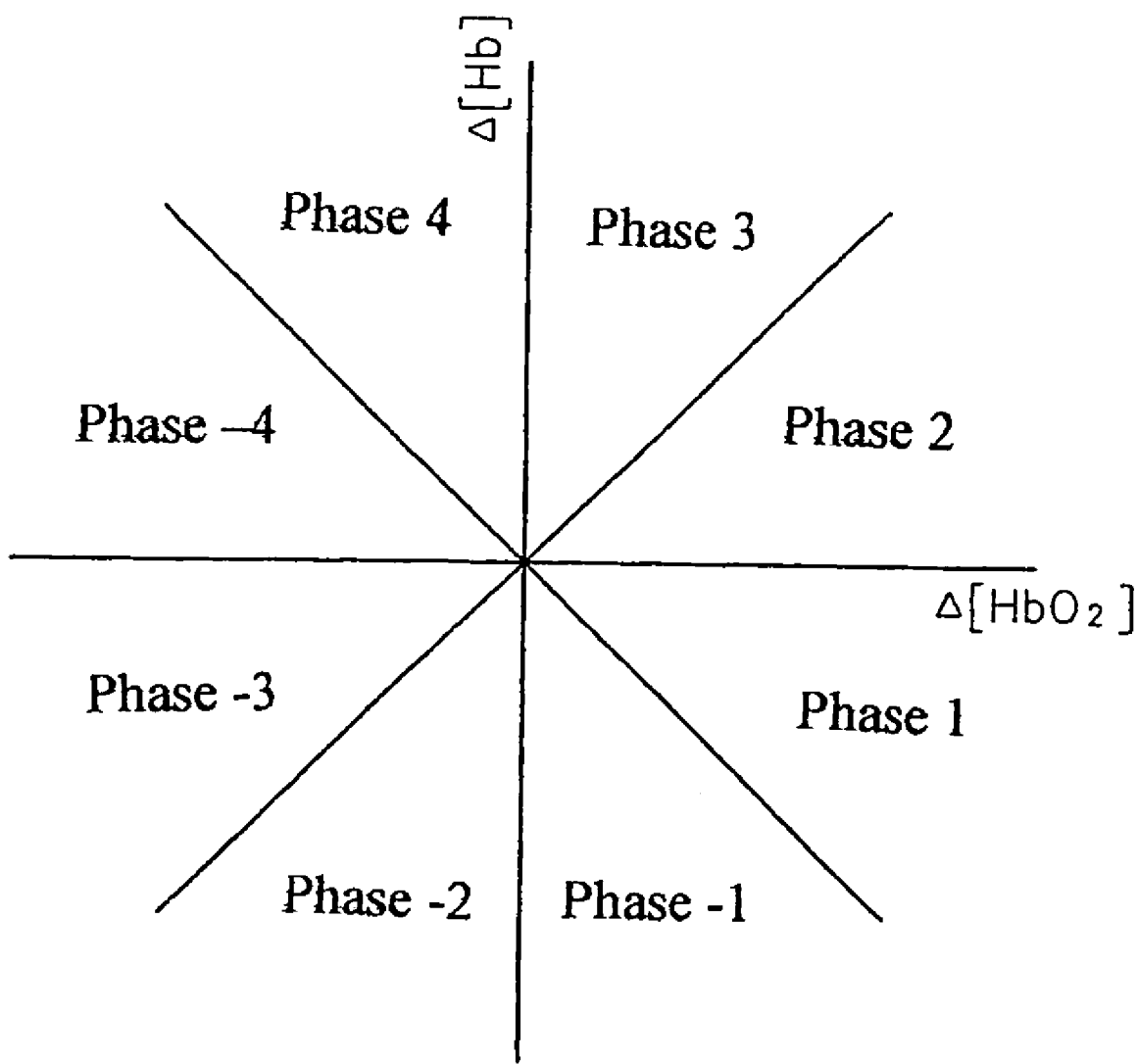
FIG. 9 shows a conceptual view of FIGS. 4 through 7 and 8(b).

The two-dimensional diagrams described thus far can be divided into phases 1 through 4 and −1 through −4, as shown in FIG. 9. When the exercise load increases, the plot locus phase changes, from 1 towards 4. Among these phases, the phases in which total hemoglobin increases the most are phases 2 and 3, when oxygenated hemoglobin and deoxygenated hemoglobin increase equally. Moving into phase 3, the increase in deoxygenated hemoglobin is greater than that of oxygenated hemoglobin, and in phase 4, oxygenated hemoglobin decreases.

Consequently, the plus phases—phases 1 through 4—are situations in which total hemoglobin is increasing.

(1) Phase 1: The brain is in a warming-up state (deoxygenated hemoglobin is washed out and replaced by oxygenated hemoglobin.

(2) Phase 2: Oxygen is conveyed to the brain by moderate exercise.

(3) Phase 3: A (competitive) athletic level of intensity.

(4) Phase 4: When this phase is sustained for very long, the regional oxygen state of the brain is impaired.

(5) Phase −4: Increased intensity may cause movement into this phase.

On the other hand, the minus phases phases −1 through −4—are situations in which total hemoglobin is decreasing.

(1) Phase −4: A region in which the brain is endangered by continuation over a long period of time. Because k values for the muscles move more easily into this phase than those of the brain, it can be said that low oxygen is handled better by the muscles.

(2) Phase −3 and phase −2: These phases are easily reached when the exercise load becomes intense, either just afterwards or in the temporary recovery process. When these phases are of long duration in the recovery process, it shows that recovery is delayed.

(3) Phase −1: Shifts easily from phase 1 into this phase at rest and while napping. Even phase −2 may be reached in deep sleep, complete relaxation or the like.

Because shifts from phase 1 through phase 4, and shifts from phase −4 through phase −1 represent the degree of contraction and expansion of the blood vessels, the advice of the person doing the evaluation to the subject is as follows, based on the properties of the phases described above.

1) Because sleep causes the phase to shift towards vessel contraction, resting time should be determined by changes in phase, and if phases 1 through 4 are not regained easily, the brain, muscles and the like should be rested until the phase returns to −1.

2) If the load on the brain causes changes only into the minus phases, without shifting into the plus phases, then failure of the brain vessels to expand is diagnosed, and the subject should be seen by a physician for diagnosis.

3) If the phase shifts to phase 4 and stays there even with a light exercise load, then a metabolic or vascular disorder is suspected, and the subject should be seen by a physician for diagnosis.

4) The basic oxygen state can be evaluated by means of the plot locus. And, the highs and lows of basic oxygen exchange variation can be evaluated by the fluctuation of the plot locus at rest. Namely, if the plot locus is circular with a low value for the above-mentioned L (distance within the phase), then because the subject's variation at rest is small, s/he should wait for L to come down when resting/recovering, to prepare for the next exercise.

5) When phase 4 or phase −4 continue, a low oxygen state occurs, and the subject should therefore stop exercising and rest. Because the subject is in a state of hypoxic ischemia in phase −3 and phase −4, s/he should wait until the phase returns to normal to allow for recovery.

6) If taking a nap causes a shift to phase −1 and phase −2, and L does not gradually become smaller, then this is a situation in which napping is not possible, and relaxation should be encouraged.

7) When exercise is resumed without the above phase changes fully returning to normal, the intensity of the load will cause phase changes to occur from an already elevated level; this case should be handled in the same way and training carried out.

8) When the phase shifts towards the upper left, as long as the subject has not fully recovered, this should be considered as a next issue, and it is necessary to wait until it returns towards the lower right.

9) When the phase shifts towards the upper right, because this is a situation in which there is increased total hemoglobin, the subject should rest until it moves lower and leftward, when total hemoglobin concentration decreases.

<Examples of Evaluation Using the Apparatus (2)>

Figure 10A:
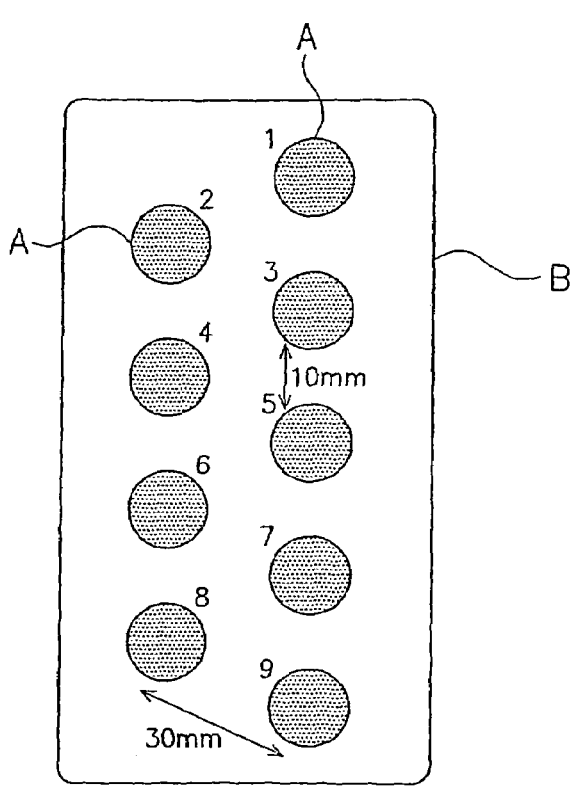
FIG. 10(a) shows a plan view of a multi-channel mounting strip, (b) shows a perspective view of that strip mounted on the head of a subject, and (c) shows diagrams on the display, obtained by plotting calculation results for each channel over time.
Figure 10B:
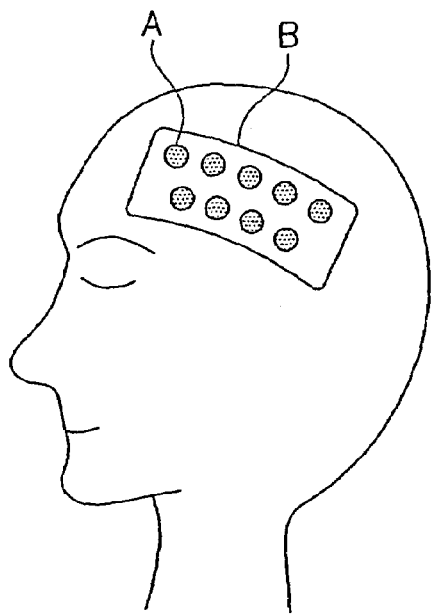

Here, a plurality (for example, 9) of multilayer probes A, already explained using FIGS. 2 and 3, are prepared, attached to a mounting strip B at suitable intervals and set on the head of a subject (FIG. 10(b)). Because multilayer probe A has selectability for data, as stated above, once measurement is started, each multilayer probe A extracts predominantly capillary data.

Figure 10C:
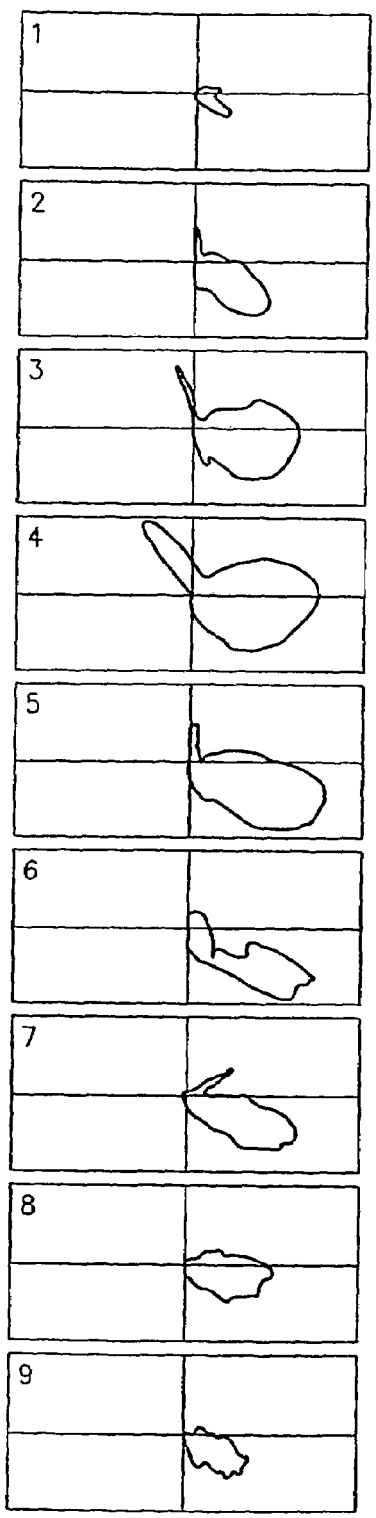

FIG. 10(c) shows two-dimensional diagrams of a situation in which the subject is spoken to (sampling during approximately 62 seconds) while accurate predominantly capillary data is being extracted from each multilayer probe A. What can be seen from this is the strength of the load received by the brain tissue (from being spoken to). From the two-dimensional diagrams from each site, it can be seen that the plot loci of the two-dimensional diagrams from probe numbers 1 through 4 become larger, and the plot loci from probe numbers 4 through 9 become smaller, and as a consequence, it can be seen that the site of probe number 4 is the region that reacts the most to words.

In this way, because the apparatus for evaluating biological function of the present working embodiment makes it possible to identify a reaction site for each type of stimulus (including both internal and external), it becomes possible to clarify the respective distribution of specific brain functions, not, as previously, the rough distribution of the fields of speech, exercise and the like, and to create a valid map of brain function. Additionally, creating this map of brain function makes it possible to evaluate whether each area of brain tissue is functioning correctly, using the apparatus for evaluating biological function of the present working embodiment.

<Other Embodiments>

The apparatus for evaluating biological function of the present invention is not limited to the working embodiment described above, and various modifications are possible within the range that does not depart from the gist of the present invention.

In the working embodiment described above, data is simultaneously collected from a plurality of measurement sites, and after decision processing is performed on each, predominantly venous data is discarded, but the present invention is not limited to this; in some cases, to understand the metabolism of biological functions, it may be necessary to continue collecting predominantly venous data as a control for predominantly capillary data. This is because venous oxygen saturation ($SvO_2$) can be determined from predominantly venous data, and capillary oxygen saturation ($ScO_2$) from predominantly capillary data using the above-mentioned Equation 9, but because, the hematocrit of the capillaries, unlike that of the veins, fluctuates easily in a living body, values for oxygen saturation for the capillaries ($ScO_2$) near the arterial side (arterial oxygen saturation ($SaO_2$)) are not necessarily higher than the values for venous oxygen saturation ($SvO_2$). Namely, the equation $ScO_2=SaO_2-SvO_2$ does not necessarily hold true. It is consequently necessary to find out $ScO_2$ directly from highly precise capillary information.

Additionally, the working embodiment described above concerns oxygenated hemoglobin and deoxygenated hemoglobin, but by means of similar techniques it is possible to determine changes in concentration of the cellular enzyme cytochrome a,a3 (cytochrome C oxidase), which is found only in cells (tissue) of living bodies, and use this as a diagnostic material. To determine changes in cytochrome a,a3 concentration, 830 nm near infrared light is provided as a new light irradiation means. Because the relationship between changes in the concentration of cytochrome a,a3 and changes in the concentration of oxygenated hemoglobin and deoxygenated hemoglobin is represented by Equation 15, the change in concentration of cytochrome a,a3 (cyt. a,a3) can be determined by means of simultaneous Equations 3 and 4.

$$\Delta O.D._{830}=a3\Delta[HbO_2]+a_3'\Delta[Hb]+a_3'' \Delta[cyt.a,a3] \quad \text{(Equation 15)}$$

where $\Delta O.D._{830}$ is change in absorbance at 830 nm wavelength, $\Delta[cyt. a,a3]$ is change in cytochrome a,a3 concentration, and $a_3$, $a_3'$, and $a_3''$ are absorbance coefficients.

Then, a new evaluation index can be established by newly adding the concept of $\Delta[cyt. a,a3]$. Deriving from the fact that stimulation of tissue causes energy to be consumed in the tissue, there is a correlation between cytochrome a,a3, which is concerned in the production of the energy metabolism enzyme ATP, and oxygenated hemoglobin, which is concerned in stimulus. Accordingly, controller 7 calculates the relevant evaluation index (referred to below as the "tissue cytochrome oxygen exchange ratio" or "k'") by means of Equation 16.

$$k'=\Delta[cyt.a,a3]/\Delta[HbO_2] \quad \text{(Equation 16)}$$

where:

k' is the tissue cytochrome oxygen exchange ratio.

When the supply of oxygen to the tissue becomes insufficient, changes occur in cytochrome a,a3. This means that if a two-dimensional diagram representation of the plot of values for k' is used, it is possible to track the process of the return to normal of energy metabolism in the cells.

Additionally, the apparatus for evaluating biological function of the present invention is not limited to brain tissue and it can be applied to any site in a living body, but when brain measurements are performed, it is possible to create and display topographies of the distribution of blood flow, hemoglobin, oxygen concentration, internal or external) stimulus application and the like by setting a plurality of multichannelized probes at specified intervals over the entire region or a partial region of the brain surface. Because the apparatus for evaluating biological function of the present invention can obtain information that accurately reflects information about brain tissue without noise, it makes it possible to perform high quality, high precision monitoring by establishing a means of displaying topography.

And, it is not an essential condition of the apparatus for evaluating biological function of the present invention that it displays diagrams; it may, for example, (1) display k values as a chronological table, or (2) display k values in real time. Or, it may (3) display both these and diagrams. It may also (4) display differentials of k values (k angular velocity) and differentials of differentials of k values (k angular acceleration) as time series graphs; it may (5) display two-dimensional diagrams with either k values, k angular velocity or k angular acceleration as the horizontal axis and any of change in total hemoglobin concentration, change in deoxygenated hemoglobin concentration or change in oxygenated hemoglobin concentration as the vertical axis; it may (6) display two-dimensional diagrams with differentials of change in oxygenated hemoglobin concentration as the horizontal axis and differentials of change in reduced oxygenated hemoglobin concentration as the vertical axis; the essential thing is that regardless of the display mode, if information concerning k values can be displayed over time, then it is within the range of the intention of the present invention, because it becomes possible to identify predominantly capillary data and evaluate biological function. When diagrams are displayed, they are not limited to two-dimensional diagrams; they may also be, for example, three-dimensional diagrams to which a time element is added (i.e., a time axis added to the plane axes of oxygenated hemoglobin concentration (change) and deoxygenated hemoglobin concentration (change)).

As other information, it may also (1) display L values (distance within the phase) differentials of L (velocity of shifts within the phase) or differentials of differentials of L (acceleration of shifts within the phase) as time series tables; or it may (2) display two-dimensional diagrams with L values, differentials of L values, or differentials of differentials of L values as the horizontal axis, and any of change in total hemoglobin concentration, change in deoxygenated hemoglobin concentration or change in oxygenated hemoglobin concentration as the vertical axis.

Figure 11A:
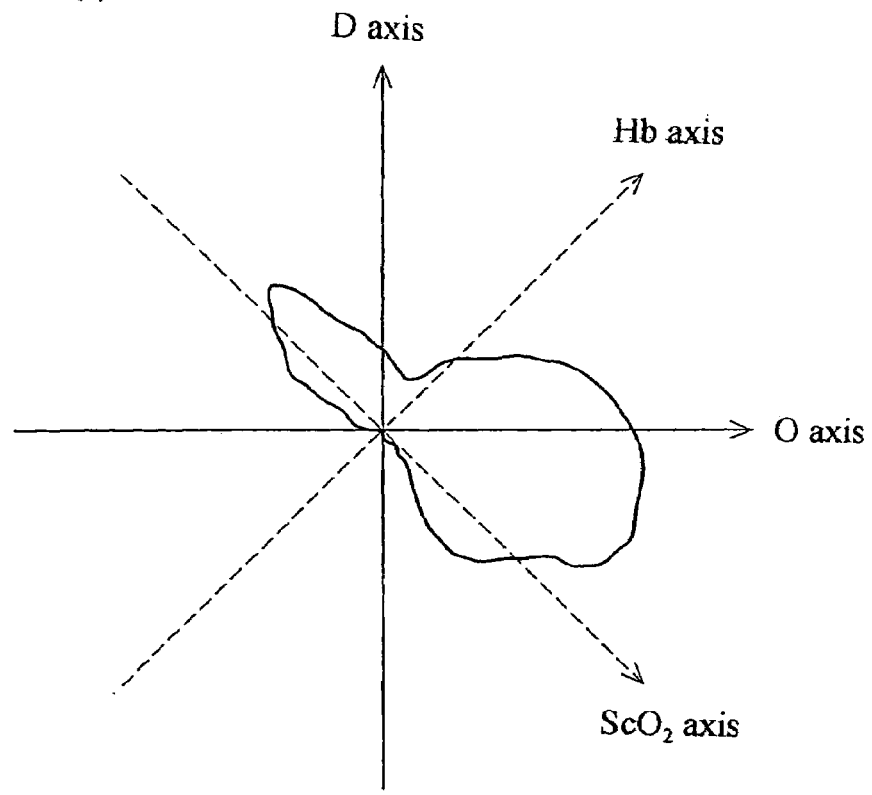
FIG. 11(a) shows a diagram on the display obtained by plotting calculated results over time (D–O coordinate system), and (b) shows a diagram of (a) rotated –45 degrees (Hb-ScO$_2$ coordinate system).
Figure 11B:
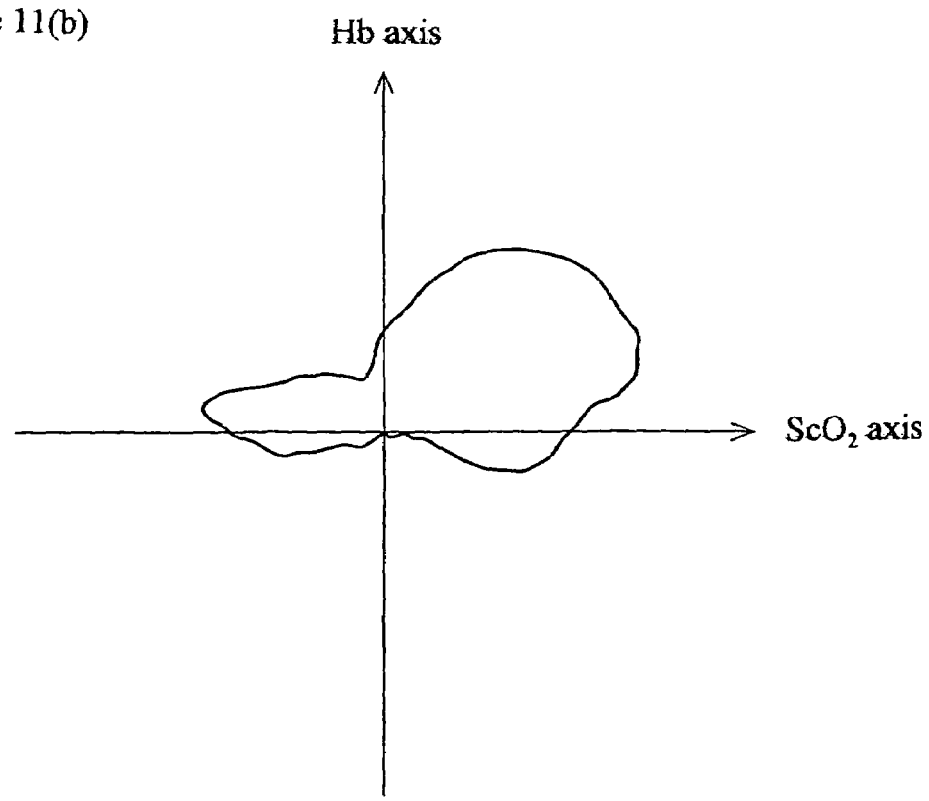

It may also extract vector components of variation in the change in capillary oxygen saturation and the change in hemoglobin concentration from both k and L values and measure the time ranges and regions showing capillary maximum oxygen saturation and minimum capillary oxygen saturation, display time series displays, topographies and the like, and compare distribution maps of changes in capillary oxygen saturation and changes in hemoglobin concentration. As shown in FIG. 11, in an above-mentioned two-dimensional diagram (FIG. 11($a$)) with changes in oxygenated hemoglobin concentration as the X-axis (horizontal axis) (O axis) and changes in deoxygenated hemoglobin concentration as the Y-axis (vertical axis) (D axis), it becomes that the axis established at 45 degrees (Hb axis) shows the change in concentration of total hemoglobin, and the axis established at −45 degrees ($ScO_2$ axis) shows the capillary oxygen saturation. Accordingly, if the coordinate system of FIG. 11($a$) is transformed by 45 degrees, it becomes a two-dimensional diagram (FIG. 11($b$)) with capillary oxygen saturation as the x axis (horizontal axis) ($ScO_2$ axis) and change in total hemoglobin concentration as the y axis (vertical axis) (Hb axis). According to the coordinate system of this FIG. 11($b$), the coordinate value on the $ScO_2$ axis of the line parallel to the Hb axis and tangent to the plot locus becomes the maximum oxygen saturation, and the time course of oxygen saturation in the capillaries can be measured even more accurately.

Additionally, the above-stated Equations 1 through 6, which form the premise for determining values for k, are only the most precise arithmetic expressions at the present point in time, and it is impossible to judge whether they will continue to be used universally in the future. It is consequently probable that there may be more precise arithmetic expressions available in the future, and in those cases those arithmetic expressions will naturally be used in determining values for k.

In addition, in the above-mentioned working embodiments, light of two wavelengths, 730 nm and 850 nm, and, with the addition of 830 nm if cytochrome is included, light of three wavelengths is used, but it goes without saying that the present invention is not limited to these wavelengths.

The invention claimed is:

1. An apparatus for evaluating biological function comprising:

light irradiation means for irradiating light to a specified site of a living body;

light detection means for detecting light exiting from the living body;

calculation means for determining respective changes in concentration of oxygenated hemoglobin and deoxygenated hemoglobin by performing calculations in near infrared spectroscopy on the intensity of the light detected by said light detection means, and for calculating a parameter for deciding whether the concentration of oxygenated hemoglobin and deoxygenated hemoglobin of said specified site of the living body are predominantly capillary data, based on said respective changes in concentration of oxygenated hemoglobin and deoxyenated hemoglobin;

decision means for deciding whether the concentration of oxygenated hemoglobin and deoxygenated hemoglobin of said specified site of the living body are predominantly capillary data by means of said calculated parameter; and display means for displaying information concerning said parameter over time.

2. An apparatus for evaluating biological function according to claim 1, wherein said light detection means detects light exiting from the living body at a plurality of detection sites, and said calculation means performs the function of determining the respective changes in concentration of oxygenated hemoglobin and deoxygenated hemoglobin for each detection site.

3. An apparatus for evaluating biological function according to claim 1, wherein said parameter is the oxygen exchange ratio "k" calculated according to the equation:

$$k = \frac{\left(\begin{array}{c}\text{change in concentration of}\\\text{deoxygenated hemoglobin}\end{array}\right)}{\left(\begin{array}{c}\text{change in concentration}\\\text{of oxygenated hemoglobin}\end{array}\right)}$$

and said decision means performs the function of deciding that the concentration of oxygenated hemoglobin and deoxygenated hemoglobin of said specified site of the living body are predominantly capillary data when said oxygen exchange ratio "k" satisfies the condition:

$k \leq -0.8$.

4. An apparatus for evaluating biological function according to claim 3, wherein said calculation means performs the function of calculating the angular velocity of said oxygen exchange ratio "k" as the differentials of said oxygen exchange ratio "k," and the angular acceleration of said oxygen exchange ratio "k" as the differentials of the differentials of said oxygen exchange ratio "k."

5. An apparatus for evaluating biological function according to claim 4, wherein said display means performs the function of displaying a two-dimensional diagram plotted overtime, with the changes in concentration of oxygenated hemoglobin as the X-axis and the changes in concentration of deoxygenated hemoglobin as the Y-axis.

6. An apparatus for evaluating biological function according to claim 5, wherein said calculation means performs the function of calculating values for "L," the differentials of said values "L," and the differentials of the differentials of said values "L," where "L" is the distance from the zero point to a plot on said two-dimensional diagram.

7. An apparatus for evaluating biological function according to claim 5, wherein said display means performs the function of displaying said two-dimensional diagram showing the relationship between changes in oxygenated hemoglobin concentration and changes in deoxygenated hemoglobin concentration rotated 45 degrees, converting said diagram into a two-dimensional diagram showing the relationship between changes in oxygen saturation and changes in total hemoglobin concentration.

8. An apparatus for evaluating biological function according to claim 7, wherein said display means performs the function of dividing said two-dimensional diagram into eight phases of 45 degrees each to display changes in phase.

9. An apparatus for evaluating biological function according to claim 8, wherein said calculation means performs the function of calculating changes in phase on said two-dimensional diagram.

10. An apparatus for evaluating biological function according to claim 1, further comprising selection means for invalidating detection sites for which the concentration of oxygenated hemoglobin and deoxygenated hemoglobin are determined not to be predominantly capillary data.

* * * * *